(12) United States Patent
Ishida

(10) Patent No.: US 7,632,942 B2
(45) Date of Patent: Dec. 15, 2009

(54) PROCESS FOR PRODUCING CYCLOALKANOL AND/OR CYCLOALKANONE

(75) Inventor: Hajime Ishida, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 472 days.

(21) Appl. No.: 11/183,920

(22) Filed: Jul. 19, 2005

(65) Prior Publication Data

US 2006/0020149 A1 Jan. 26, 2006

(30) Foreign Application Priority Data

Jul. 22, 2004 (JP) ............... 2004-214122

(51) Int. Cl.
C07C 29/48 (2006.01)
C07B 47/00 (2006.01)
(52) U.S. Cl. .................. 540/145; 568/835
(58) Field of Classification Search ........... 540/145; 568/835
See application file for complete search history.

(56) References Cited

U.S. PATENT DOCUMENTS

| 3,855,307 A | 12/1974 | Rony et al. | |
| 3,957,876 A | 5/1976 | Rapoport et al. | |
| 5,004,837 A * | 4/1991 | Baur et al. | 568/342 |
| 5,672,778 A * | 9/1997 | Lyons et al. | 568/835 |
| 5,767,320 A | 6/1998 | Raja et al. | |

FOREIGN PATENT DOCUMENTS

| CN | 1269343 A | 10/2000 |
| EP | 0453021 A1 * | 10/1991 |
| EP | 0 471 561 A2 | 2/1992 |
| EP | 0 532 326 A2 | 3/1993 |
| EP | 0 532 327 A2 | 3/1993 |
| EP | 0 704 447 A1 | 4/1996 |

OTHER PUBLICATIONS (Note—2 references by this author): Nam et al. (1) Tetrahedron Letters 43 (2002) 5487-5490 "Sterioselective alkane . . ." (2) Chem. Commun., 2001, 1262-1263, "Biomimetic alkane hydroxylation . . .".*
Haber et al., "cationic metalloporphyrins . . . ", J. of Molecular Catalysis A: Chemical 224 (2004) 153-159.*
Guo et al., Effective catalysis . . . , Applied Catalysis A General 246 (2003) 303-309.*
Murashashi et al., "Metalloporphyrin-Catalyzed Oxidation of Alkanes . . . ", Tetrahedron Letters, vol. 36, No. 44, pp. 8059-8062, 1995.*
C. Guo et al., "Effect catalysis of simple metalloporphyrins for cyclohexane oxidation with air in the absence of additives and solvents", Applied Catalysis A: General 246, (2003), (XP-002360226), pp. 303-309.
W. Nam et al., "Biomimetic alkane hydroxylation by cobalt (ω) porphyrin complex and m-chloroperbenzoic acid", Chem. Commun., 2001, (XP-002360227), pp. 1262-1263.

* cited by examiner

*Primary Examiner*—James O. Wilson
*Assistant Examiner*—Paul V. Ward
(74) *Attorney, Agent, or Firm*—Sughrue Mion, PLLC

(57) ABSTRACT

The object of the present invention is to produce cycloalkanol and/or cycloalkanone with good selectivity by oxidizing cycloalkane with molecular oxygen. The method of the present invention contains the step of oxidizing cycloalkane with molecular oxygen in the presence of cobalt salt of carboxylic acid and cobalt complex with porphyrin as a ligand, the cobalt complex with porphyrin as a ligand being a compound represented by the formula (1):

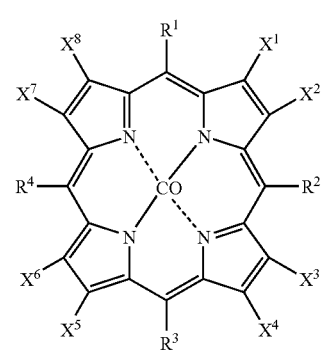

(1)

wherein each of $X^1$ to $X^8$ independently represents a hydrogen atom, a halogen atom, a nitro group, a cyano group, a hydrocarbon group, a halogenated hydrocarbon group or a sulfonyl group, and each of $R^1$ to $R^4$ independently represents a hydrogen atom, a nitro group, a cyano group, a hydrocarbon group or a halogenated hydrocarbon group.

3 Claims, No Drawings

PROCESS FOR PRODUCING CYCLOALKANOL AND/OR CYCLOALKANONE

BACKGROUND OF THE INVENTION

1. Field of the Invention

The present invention relates to a process for producing cycloalkanol and/or cycloalkanone by oxidizing cycloalkane with molecular oxygen.

2. Description of the Related Art

As a method for oxidizing hydrocarbon such as alkane, cycloalkane and alkene with molecular oxygen, there has been known a method utilizing cobalt salt of carboxylic acid as a catalyst (e.g., see U.S. Pat. No. 3,957,876). In addition, recently, a method utilizing porphyrin complex as a catalyst has been proposed. As a such catalyst, for instance, EP 0 471 501 A discloses a complex of iron, chromium, manganese, ruthenium or copper with perhalogenated porphyrin as a ligand; EP 0 532 327 A discloses a complex of iron, chromium, manganese, ruthenium, cobalt or copper with cyanated porphyrin as a ligand; EP 0 532 326 A discloses a complex of iron, chromium, manganese, ruthenium, cobalt or copper with nitrated porphyrin as a ligand; and EP 0 704 447 A discloses a complex of iron with halogenated porphyrin as a ligand.

SUMMARY OF THE INVENTION

However, the sufficient selectivity of a product, for example the selectivity of cycloalkanol and/or cycloalkanone produced by oxidizing cycloalkane with molecular oxygen, has not been achieved by those previous methods described above.

The present invention provides a process for producing cycloalkanol and/or cycloalkanone by oxidizing cycloalkane with molecular oxygen in the presence of cobalt salt of carboxylic acid and cobalt complex with porphyrin as a ligand.

According to the present invention, cycloalkanol and/or cycloalkanone can be produced from cycloalkane with good selectivity.

DETAILED DESCRIPTION OF THE PREFERRED EMBODIMENT

In the present invention, cycloalkane is used as a starting material, which is oxidized with molecular oxygen in the presence of a catalyst to produce corresponding cycloalkanol and/or cycloalkanone.

Examples of the cycloalkane as the starting material include monocyclic cycloalkane with no substituent on the ring, such as cyclopropane, cyclobutane, cyclopentane, cyclohexane, cycloheptane, cyclooctane, cyclodecane and cyclooctadecane; polycyclic cycloalkane such as norbornane, decalin and adamantane; cycloalkane with a substituent on the ring, such as methylcyclopentane and methylcyclohexane; and the like, which usually have about 3 to 20 carbon atoms. Two or more of them can be used together, if necessary.

Oxygen-containing gas is usually used as a source of the molecular oxygen. The oxygen-containing gas may be air or pure oxygen, or may be diluted air or pure oxygen with an inert gas such as nitrogen, argon, or helium. Alternatively, oxygen-enriched air, which can be obtained by adding pure oxygen to the air, may be used as the oxygen-containing gas.

In the present invention, cobalt salt of carboxylic acid (hereinafter, it may be referred to as cobalt salt) and cobalt complex with porphyrin as a ligand (hereinafter, it may be referred to as cobalt complex) are used together as catalysts for oxidizing cycloalkane with molecular oxygen. By employing such catalyst system, cycloalkane can be oxidized and cycloalkanol and/or cycloalkanone can be produced with good selectivity.

The cobalt salt used in the present invention may be a salt of monohydric or polyhydric aliphatic carboxylic acid, alicyclic carboxylic acid or aromatic carboxylic acid. Two or more of them can be used together, if necessary. Preferred examples of the cobalt salt include cobalt acetate, cobalt 2-ethylhexanoate, cobalt naphthoate, cobalt oxalate, cobalt laurate, cobalt palmitate, cobalt stearate and the like. The cobalt salt is preferably a salt of aliphatic carboxylic acid, more preferably a salt of aliphatic carboxylic acid having 2 to 20 carbon atoms, and further preferably a salt of aliphatic carboxylic acid having 6 to 10 carbon atoms.

Another catalyst component, cobalt complex is typically represented by the following formula (1):

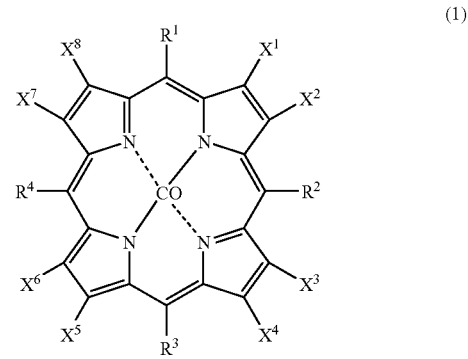

(wherein, each of $X^1$ to $X^8$ independently represents a hydrogen atom, a halogen atom, a nitro group, a cyano group, a hydrocarbon group, a halogenated hydrocarbon group or a sulfonyl group, each of $R^1$ to $R^4$ independently represents a hydrogen atom, a nitro group, a cyano group, a hydrocarbon group or a halogenated hydrocarbon group.)

In the formula (1), when at least one of $X^1$ to $X^8$ existing on the pyrrole ring is a halogen atom, the halogen atom can be a fluorine atom, a chlorine atom, a bromine atom or an iodine atom. When at least one of $X^1$ to $X^8$ is a hydrocarbon group, the hydrocarbon group can be an aliphatic hydrocarbon group, an alicyclic hydrocarbon group or an aromatic hydrocarbon group.

As used herein, an aliphatic hydrocarbon group is a residue of aliphatic hydrocarbon whose hydrogen atom is removed therefrom, which usually has about 1 to 20 carbon atoms. Specific examples of the aliphatic hydrocarbon group include an alkyl group such as a methyl group, an ethyl group, an n-propyl group, an isopropyl group, an n-butyl group, an isobutyl group, a s-butyl group and a t-butyl group; an alkenyl group such as a vinyl group, an allyl group, and a methallyl group; an alkynyl group such as an ethynyl group and a propargyl group; and the like.

An alicyclic hydrocarbon group is a residue of alicyclic hydrocarbon whose hydrogen atom is removed therefrom, which usually has about 3 to 20 carbon atoms. The alicyclic hydrocarbon group may be the residue of alicyclic hydrocarbon whose hydrogen atom on the aliphatic ring is removed therefrom or may be the residue of alicyclic hydrocarbon having aliphatic chain whose hydrogen atom on the aliphatic chain is removed therefrom. Specific examples of the alicyclic hydrocarbon group include a cycloalkyl group such as a cyclopropyl group, a cyclobutyl group, a cyclopentyl group and a cyclohexyl group; a cycloalkyl alkyl group such as a cyclopentylmethyl group and a cyclohexylmethyl group; and the like.

An aromatic hydrocarbon group is a residue of aromatic hydrocarbon whose hydrogen atom is removed therefrom, which usually has about 6 to 20 carbon atoms. The aromatic hydrocarbon group may be the residue of aromatic hydrocarbon whose hydrogen atom on the aromatic ring is removed therefrom, or may be the residue of aromatic hydrocarbon having aliphatic chain whose hydrogen atom on the aliphatic chain is removed therefrom, or may be the residue of aromatic hydrocarbon having aliphatic ring whose hydrogen atom on the aliphatic ring is removed therefrom. Specific examples of the aromatic hydrocarbon group include an aryl group such as a phenyl group, a tolyl group and a naphthyl group; an arylalkyl group (an aralkyl group) such as a benzyl group and a phenethyl group; and the like.

When at least one of $X^1$ to $X^8$ is a halogenated hydrocarbon group, the halogenated hydrocarbon group can be a hydrocarbon group on which at least one hydrogen atom is substituted with a fluorine atom, a chlorine atom, a bromine atom or an iodine atom. When at least one of $X^1$ to $X^8$ is a sulfonyl group, the sulfonyl group can be a group having a hydrocarbon group bonding to unsubstituted (—$SO_2$—) group. The hydrocarbon group in those halogenated hydrocarbon group and sulfonyl group can be an aliphatic hydrocarbon group, alicyclic hydrocarbon group or aromatic hydrocarbon group as in the case of the hydrocarbon group representing $X^1$ to $X^8$, and exemplified similarly as in the hydrocarbon group representing $X^1$ to $X^8$.

Whereas, in the formula (1), when at least one of $R^1$ to $R^4$ existing on carbons linking the pyrrole rings is a hydrocarbon group, the hydrocarbon group can also be an aliphatic hydrocarbon group, alicyclic hydrocarbon group or aromatic hydrocarbon group as in the case of the hydrocarbon group representing $X^1$ to $X^8$, and exemplified similarly as in the hydrocarbon group representing $X^1$ to $X^8$.

When at least one of $R^1$ to $R^4$ is a halogenated hydrocarbon group, similarly as in the halogenated hydrocarbon group representing $X^1$ to $X^8$, the halogenated hydrocarbon group can also be a hydrocarbon group on which at least one hydrogen atom is substituted with a fluorine atom, a chlorine atom, a bromine atom or an iodine atom. When at least one of $X^1$ to $X^8$ is a sulfonyl group, the sulfonyl group can also be a group having a hydrocarbon group bonding to unsubstituted (—$SO_2$—) group, similarly as in the sulfonyl group representing $X^1$ to $X^8$. Moreover, the hydrocarbon group in those halogenated hydrocarbon group and sulfonyl group can also be an aliphatic hydrocarbon group, an alicyclic hydrocarbon group or an aromatic hydrocarbon group as in the case of the hydrocarbon group representing $X^1$ to $X^8$, and exemplified similarly as in the hydrocarbon group representing $X^1$ to $X^8$.

In the formula (1), at least one of $X^1$ to $X^8$ is preferably a halogen atom, and in this occasion, preferably others than the halogen atom are a hydrogen atom, a hydrocarbon group or a halogenated hydrocarbon group, and more preferably all of $X^1$ to $X^8$ are halogen atoms. $R^1$ to $R^4$ are preferably a hydrogen atom, a hydrocarbon group or a halogenated hydrocarbon group.

Such cobalt complex represented by the formula (1) can be prepared by known methods, for example a method described in Journal of Organic Chemistry, Vol. 32, p. 476, 1967, and a method described in Inorganic Chemistry, Vol. 31, p. 2044, 1992. The cobalt complex may be used with being carried on a carrier such as silica, alumina, titania, montmorillonite, zeolite, hydrotalcite and the like.

Oxidation reaction can be conducted by contacting cycloalkane with molecular oxygen in the presence of cobalt salt and the cobalt complex. Amounts of the cobalt salt used and the cobalt complex used are, in the total amount of both, usually 0.01 to 100 ppm by weight, preferably 0.1 to 50 ppm by weight to cycloalkane. Weight ratio of the cobalt salt to the cobalt complex is usually 100:1 to 1:100, preferably 20:1 to 1:20.

An oxidation reaction temperature is usually in the range of 0 to 200° C., preferably 100 to 180° C., more preferably 130 to 180° C., further preferably 145 to 180° C. A reaction pressure is usually in the range of 0.01 to 10 MPa, preferably 0.1 to 2 MPa. A solvent can be employed in the reaction, if necessary. Examples of the solvent include a nitrile solvent such as acetonitrile and benzonitrile, and carboxylic acid solvent such as acetic acid and propionic acid, and the like.

The post treatment operation after the oxidation reaction is not particularly limited. Examples of the post treatment include a method comprising the steps of washing a reaction mixture with water to separate the cobalt salt and the cobalt complex therefrom, and then distilling the reaction product, and the like. When cycloalkyl hydroperoxide is contained in the reaction mixture, the reaction mixture may be subjected to an alkaline treatment, reduction treatment or the like, to convert the cycloalkyl hydroperoxide easily into a desired cycloalkanol or cycloalkanone.

The resulting cycloalkanol can be converted into cycloalkanone by a known method, and cycloalkanone is used as a starting material for producing oxime or lactam.

EXAMPLES

The present invention is described in more detail by following Examples, which should not be construed as a limitation upon the scope of the present invention. Analyses of cyclohexane, cyclohexanone, cyclohexanol and cyclohexyl hydroperoxide in a reaction mixture were conducted by gas chromatography. Based on results of the analysis, conversion of cyclohexane and respective selectivities to cyclohexanone, cyclohexanol and cyclohexyl hydroperoxide were determined.

Example 1

As catalysts, 0.0007 g ($2.1 \times 10^{-6}$ mol) of cobalt(II) 2-ethylhexanoate and 0.0035 g ($2.1 \times 10^{-6}$ mol) of cobalt(II) 5,10,15,20-tetrakis(pentafluorophenyl)-2,3,7,8,12,13,17,18-octabromoporphyrin (compound of the formula (1), wherein $X^1$ to $X^8$ are bromine atoms and $R^1$ to $R^4$ are pentafluorophenyl groups) were dissolved in 2499.6 g (29.7 mol) of cyclohexane to prepare feed liquid (catalyst/starting material solution). Into 1 L autoclave, 278 g of the feed liquid was introduced, and inside of the system was pressured to 0.6 MPa with nitrogen, and then, the temperature of the system was increased to 145° C. with flowing nitrogen. Continuous reaction was conducted for 4 hours with supplying the feed liquid at 4.6 g/min. with flowing air so as to make oxygen concentration in an exhaust gas 1 to 5% by volume under conditions of reaction temperature 145° C., reaction pressure 0.6 MPa, and residence time 60 minutes. From a result of analysis of the reaction mixture, a conversion of cyclohexane was 4.1%, and selectivities of cyclohexanone, cyclohexanol and cyclohexyl hydroperoxide were 27.0%, 33.3% and 30.2%, respectively (total selectivity was 90.5%).

Example 2

A procedure was conducted similarly as in Example 1, except that residence time was 75 minutes. A conversion of cyclohexane was 5.7%, and selectivities of cyclohexanone, cyclohexanol and cyclohexyl hydroperoxide were 31.4%, 34.4% and 19.2%, respectively (total selectivity was 85.0%).

Comparative Example 1

A procedure was conducted similarly as in Example 1, except that 0.0070 g (4.2×10$^6$ mol) of cobalt(II) 5,10,15,20-tetrakis(pentafluorophenyl)-2,3,7,8,12,13,17,18-octabromoporphyrin was used alone as a catalyst and cobalt(II) 2-ethylhexanoate was not used. A conversion of cyclohexane was 5.5%, and selectivities of cyclohexanone, cyclohexanol and cyclohexyl hydroperoxide were 29.4%, 38.3% and 15.7%, respectively (total selectivity was 83.4%).

Comparative Example 2

A procedure was conducted similarly as in Comparative Example 1, except that residence time was 75 minutes. A conversion of cyclohexane was 7.5%, and selectivities of cyclohexanone, cyclohexanol and cyclohexyl hydroperoxide were 31.7%, 35.7% and 10.7%, respectively (total selectivity was 78.1%).

Comparative Example 3

A procedure was conducted similarly as in Example 1, except that cobalt(II) 5,10,15,20-tetrakis(pentafluorophenyl)-2,3,7,8,12,13,17,18-octabromoporphyrin was not used and 0.0021 g (5.9×10$^{-6}$ mol) of cobalt(II) 2-ethylhexanoate was used alone as a catalyst, and a reaction pressure was 0.9 MPa. A conversion of cyclohexane was 7.0%, and selectivities of cyclohexanone, cyclohexanol and cyclohexyl hydroperoxide were 24.6%, 15.6% and 11.5%, respectively (total selectivity was 51.7%).

Comparative Example 4

A procedure was conducted similarly as in Comparative Example 3, except that residence time was 50 minutes. A conversion of cyclohexane was 6.4%, and selectivities of cyclohexanone, cyclohexanol and cyclohexyl hydroperoxide were 26.0%, 22.2% and 16.7%, respectively (total selectivity was 64.9%).

What is claimed is:

1. A process for producing cycloalkanol and/or a cycloalkanone, comprising the step of oxidizing cycloalkane with molecular oxygen in the presence of cobalt salt of carboxylic acid and cobalt complex with porphyrin as a ligand, wherein the cobalt complex with porphyrin as a ligand is a compound represented by the formula (1):

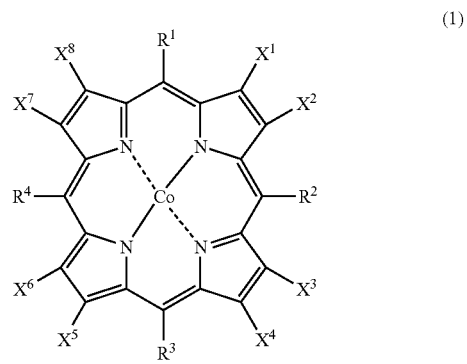

(1)

wherein each of $X^1$ to $X^8$ independently represents a hydrogen atom, a halogen atom, a nitro group, a cyano group, a hydrocarbon group, a halogenated hydrocarbon group or a sulfonyl group, and each of $R^1$ to $R^4$ independently represents a hydrogen atom, a nitro group, a cyano group, a hydrocarbon group or a halogenated hydrocarbon group.

2. The process according to claim 1, wherein at least one of the $X^1$ to $X^8$ in the formula (1) is a halogen atom.

3. The process according to claim 1 or 2, wherein the cycloalkane is cyclohexane.

* * * * *